United States Patent [19]

Bietti et al.

[11] Patent Number: 5,576,318
[45] Date of Patent: Nov. 19, 1996

[54] BENZIMIDAZOLONE DERIVATIVES

[75] Inventors: Giuseppe Bietti, Milan; Franco Borsini, Prato; Marco Turconi, Voghera; Ettore Giraldo; Maura Bignotti, both of Milan, all of Italy

[73] Assignee: Boehringer Ingelheim Italia S.p.A., Milan, Italy

[21] Appl. No.: 216,742

[22] Filed: Mar. 23, 1994

Related U.S. Application Data

[63] Continuation of Ser. No. 39,002, filed as PCT/IT92/00088, Jul. 30, 1992, abandoned.

[30] Foreign Application Priority Data

Jul. 30, 1991 [IT] Italy .................... MI91A2118

[51] Int. Cl.$^6$ .............. A61K 31/495; C07D 403/00; C07D 473/00
[52] U.S. Cl. ............... 514/253; 514/252; 544/295; 544/366; 544/370; 548/304.4; 548/304.7; 548/306.4
[58] Field of Search ............. 544/370, 366, 544/295; 514/253, 252; 548/304.4, 304.7, 306.4

[56] References Cited

U.S. PATENT DOCUMENTS

| | | | |
|---|---|---|---|
| 3,406,178 | 10/1968 | Crocker et al. | 548/304.4 |
| 3,472,854 | 10/1969 | Archer | 514/255 |
| 4,737,500 | 4/1988 | Sorg | 514/252 |
| 4,797,399 | 1/1989 | Ueda et al. | 544/370 |
| 4,859,692 | 8/1989 | Bernstein et al. | 548/304.4 |
| 4,886,803 | 12/1989 | Sueda et al. | 544/370 |
| 4,940,793 | 7/1990 | Botre et al. | 544/370 |
| 4,954,503 | 9/1990 | Strupczewski et al. | 514/254 |
| 5,036,088 | 7/1991 | Kitaura et al. | 544/370 |

FOREIGN PATENT DOCUMENTS

| | | |
|---|---|---|
| 904945 | 12/1986 | Belgium . |
| 200322 | 11/1986 | European Pat. Off. . |
| 526434 | 2/1993 | European Pat. Off. . |
| 023594 | 1/1980 | United Kingdom . |

OTHER PUBLICATIONS

Damour et al. CA 118–124537e (1992).
Awouters et al, CA88–98788(1977).
Vaudenberk et al. CA88–50920n (1977).

*Primary Examiner*—Cecilia Tsang
*Attorney, Agent, or Firm*—R. P. Raymond; M-E. M. Devlin; A. R. Stempel

[57] ABSTRACT

Pharmacologically active benzimidazolone derivatives as 5-HT$_{1A}$ and 5-HT$_2$ receptors, useful in the treatment of CNS disorders, of formula:

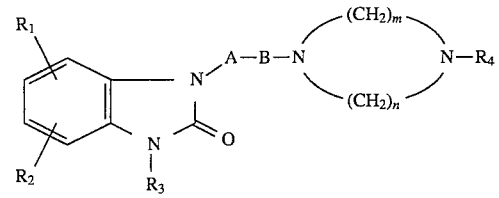

wherein the substituents are defined herein.

6 Claims, No Drawings

BENZIMIDAZOLONE DERIVATIVES

This is a continuation of application Ser. No. 08/039,002, filed as PCT/IT92/00088, Jul. 30, 1992 now abandoned.

The present invention relates to novel pharmacologically active benzimidazolone derivatives and acid addition salts thereof, to processes for their preparation and to pharmaceutical compositions containing them. The new compounds possess central serotonergic activity and are useful in the treatment of central nervous system (CNS) disorders.

It is known that 1 A and 2 serotonergic receptors ($5\text{-}HT_{1A}$ and $5\text{-}HT_2$) seem to be important for many functions in the animal body. For instance, altered function of these receptors is involved in the genesis and/or treatment of anxiety, depression, psychoses, abnormality of sleep and feeding, organic mental diseases and alteration of blood pressure. In spite of the clear involvement of $5\text{-}HT_{1A}$ receptors in such a huge amount of pathological events, it is not clear why, for example, some compounds acting upon $5\text{-}HT_{1A}$ receptors exert in humans a preferential anxiolytic effects, while others exert a preferential hypotensive action. The same holds for $5\text{-}HT_2$ antagonists. This is probably due to heterogeneous characteristics, so far unknown, of $5\text{-}HT_{1A}$ and $5\text{-}HT_2$ receptors. Therefore, there is the possibility that compounds acting on $5\text{-}HT_{1A}$ and $5\text{-}HT_2$ receptors may exert a wide range of therapeutic effects in humans.

GB 2023594 describes a class of 1-substituted alkyl-4-(3-trifluoromethylthiophenyl)-piperazines which may contain, as a substituent of the alkyl group, an optionally 3-substituted benzimidazolone groupment. The above compounds were found to exert activity in the central nervous system, which was showed by behavioural tests in mice. The benzimidazolone groupment was also used as a generic substituent in the preparation of structurally different classes of compounds endowed with activity on the central nervous system; examples may be found in BE 904,945, U.S. Pat. No. 4,954,503 and EP 200,322. U.S. Pat. No. 3,472,854 describes (benzimidazolyl)-lower alkyl substituted piperazines useful, among other indications, as tranquillisers and sedatives. EP 0376607 describes piperazinylbutyl indole derivatives, including 2-indolones, which have been found to possess central serotonergic activity with preference for the $5\text{-}HT_{1A}$ receptor subtype. WO 92/19606 describes a class of heterocyclicderivatives, including benzimidazolinonederivatives which were found to have serotonergic activity, preferably for the $5\text{-}HT_2$ receptor. We have now synthetised, and this is the object of the present invention, a novel class of structurally distinct compounds showing affinity for the $5\text{-}HT_{1A}$ and $5\text{-}HT_2$ receptors. These new compounds may be useful in the treatment of CNS diseases such as affective disorders, (for example depression and bipolar disorders), anxiety, sleep and sexual disorders, psychosis, schizophrenia, personality disorders, mental organic disorders and mental disorders in childhood, aggressiveness, age associated memory impairment.

Moreover they may be used for cardiovascular disorders such as hypertension and thrombosis.

According to the present invention we provide compounds of general formula (I)

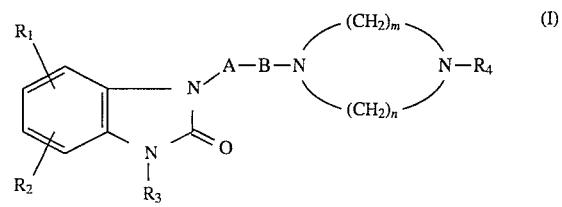

where $R_1$ and $R_2$ may be at the same time or not a hydrogen atom, halogen, trifluoromethyl, $C_{1-6}$ alkyl, $C_{1-6}$ alkoxy, $C_{1-6}$ alkylthio, $C_{1-6}$ acyl, carboxyl, $C_{1-6}$ alkoxycarbonyl, hydroxy, nitro, amino optionally $C_{1-4}$ alkyl N-mono or di-substituted, $C_{1-6}$ acylamino, $C_{1-6}$ alkoxycarbonylamino, carbamoyl optionally $C_{1-4}$ alkyl N-mono or di-substituted, cyano, $C_{1-6}$ alkylsulphinyl, $C_{1-6}$ alkylsulphonyl, amino sulphonyl optionally $C_{1-4}$ alkyl N-mono or di-substituted, $C_{1-4}$ alkyl N-mono or di-substituted aminosulphonylamino, aminosulphonylamino;

$R_3$ is hydrogen, $C_{1-6}$ alkyl, $C_{2-6}$ alkenyl or $C_2$-$C_6$ alkynyl;

A is —CO— or —CONH— or it is absent;

B is a straight or branched, saturated or unsaturated $C_{2-6}$ alkyl;

m and n are both independently an integer from 1 to 3;

$R_4$ is an aryl, aralkyl, a heteroaryl or heteroaralkyl group, each group being optionally substituted by one or more substituents selected from halogen, trifluoromethyl, cyano, $C_{1-3}$ alkoxy, $C_{1-4}$ alkyland acid addition salts thereof.

For pharmaceutical use the compounds of general formula (I) may be used as such or in the form of tautomers or of physiologically acceptable acid addition salts thereof. The term "acid addition salts" includes salts either with inorganic or organic acids. Physiologically acceptable organic acids which may be used in salt formation include, for example, maleic, citric, tartaric, fumaric, methansulphonic, acetic, benzoic, succinic, gluconic, isethionic, glycinic, lactic, malic, mucoic, glutammic, sulphamic and ascorbic acid; suitable inorganic acids include hydrochloric, hydrobromic, nitric, sulfuric or phosphoric acid.

Some of the compounds of formula (I) according to the present invention contain chiral or prochiral centres and thus may exist in different stereoisomeric forms including enantiomers of (+) and (−) type or mixtures of them. The present invention includes in its scope both the individual isomers and the mixtures thereof.

It has to be understood that, when mixtures of optical isomers are present, they may be separated according to the classic resolution methods based on their different physico-chemical properties, e.g. by fractional crystallization of their acid addition salts with a suitable optically active acid or by the chromatographic separation with a suitable mixture of solvents.

When in the compounds of formula (I) $R_1$, $R_2$ and $R_3$ represent $C_{1-6}$ alkyl group, such groups refer to an alkyl group having a straight or branched chain. Typical groups of that kind include methyl, ethyl, n-propyl, i-propyl, n-butyl, t-butyl, n-hexyl, 2-methylpentyl and the like. The term halogen means fluoro, chloro, bromo and jodio. Preferred halogens are fluoro, chloro and bromo and particularly fluoro and chloro. When $R_1$ and $R_2$ represent a $C_{1-6}$ alkoxy group, they may, for example, be methoxy, ethoxy, propoxy, butoxy, pentoxy, hexyloxy. When $R_1$ and $R_2$ represent a $C_{1-6}$ acyloxy group it may, for example, be acetoxy, propionyloxy. When B is a straight or branched, saturated or unsaturated $C_{2-6}$ alkyl group, it may, for example, ethyl, propyl, butyl, hexyl, 2-methylpropyl, 2-butenyl.

When $R_4$ is aryl, aralkyl it may, for example, be phenyl, benzyl or naphtyl respectively, each group being optionally substituted by one or more substituents selected from fluoro, chloro, methoxy, methyl, trifluoromethyl, ethyl, ethoxy. When $R_4$ is heteroaryl or heteroalkyl, it may, for example, be 1,2-benzisothiazole, benzodioxane, pyrimidine or 1,2-benzioxazole.

When m and n are one of integers from 1 to 3, there may, for example, form a saturated 5-7-membered heterocyclic ring, such as piperazine, imidazolidine, diazepine.

Preferred compounds according to the present invention are those wherein A is absent, B is a straight, saturated $C_{2-4}$ alkyl, m and n are the integer 2. $R_4$ is a substituted phenyl ring wherein the substituents are selected from methoxy, chloro and trifluoromethyl.

The compounds of the general formula (I) may conveniently be prepared by a variety of synthetic routes using conventional methods. According to a further feature of the invention we provide processes for the preparation of compounds of formula I as hereinbefore described in which either a) a compound of general formula (II)

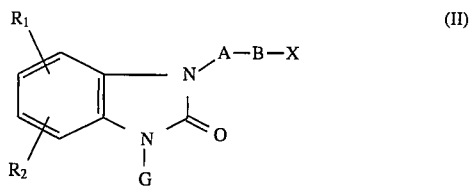

wherein G is $R_3$, or it is a protecting group selected from alkoxycarbonyl, aryloxycarbonyl, arylalkenyl, alkylalkenyl group, preferably ethoxycarbonyl, A-methylvinyl, A-phenylvinyl, A is absent, $R_1$, $R_2$, $R_3$ and B are as hereinbefore defined and X is a leaving group such as halogen, methansulfonate or 4-methylbenzensulfonate, is reacted with a compound of formula (III)

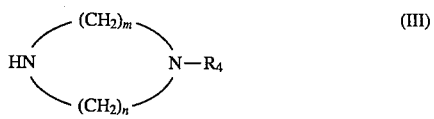

wherein $R_4$, m and n are as hereinbefore defined. The reaction may be conveniently carried out in solvents such as alcohols, ketones, benzene, ethyl acetate, acetonitrile, dioxane, chloroform, dimethylformamide at a temperature ranging from 0° C. to 150° C., preferably at 5° C. or at the boiling point of the same solvent. The presence of an acid acceptor such as sodium carbonate, triethylamine and the like may be useful. When G represents an alkoxy- or aryloxy-protecting group, it may be either conveniently removed during the process or it may be cleared by subsequent treatment with aqueous alkaly such as diluted sodium hydroxyde, diluted potassium hydroxyde, sodium or potassium carbonate, sodium or potassium hydrogencarbonates; in the case G is arylalkenyl or alkylalkenyl group it may be removed by subsequent treatment with acids such as aqueous hydrochloric or sulphuric acid; in every instance choice products of general formula (I) in which $R_3$ is H are obtained.

The compounds of general formula (II), used as starting materials in the above mentioned process, may be prepared by reacting a compound of general formula (IV)

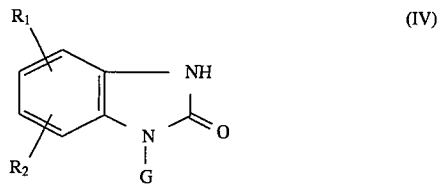

wherein $R_1$, $R_2$ and G are as hereinbefore defined, with an alkyldihalide or a haloalkanole in the presence of a strong base, such as sodium hydride in an aprotic solvent such as tetrahydrofurane or dimethylformamide, or solid potassium hydroxyde in dimethylformamide at a temperature ranging from 20° C. and 100° C., or in the presence of aqueous alkali such as sodium or potassium hydroxide in the presence of an organic solvent unsoluble with water, such as methylene chloride, benzene or toluene and in the presence of a catalytic amount of an phase transfer catalyst such as ammonium quaternary salt, at a temperature ranging from 20° C. and the boiling point of the same solvent. When a haloalkanol is used, the hydroxyl group of the obtained product is changed into methansulfonate or 4-methylbenzensulfonate by the treatment with methansulfonylchloride or with 4-methylbenzensulfonylchloride to give the compound of general formula III. The compounds of general formula IV may in turn be prepared by methods known in the literature such as for example those exemplified in J. Org. Chem. 38, 3498–502 (1973); or b) compound of general formula (V)

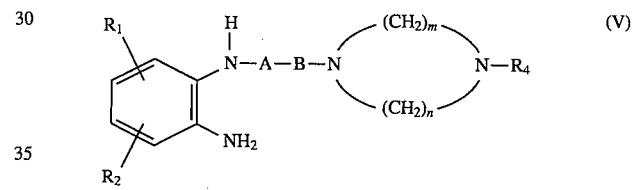

wherein $R_1$, $R_2$, $R_4$, A, B, m and n are as hereinbefore defined, is reacted with a carbonyl derivative of formula (VI)

wherein Y and Y' are leaving groups identical or different from each other such as halogen, halogenated alkoxy, alkoxy, aryloxy or heterocycle. Preferred groups are chlorine, trichloromethoxy, methoxy, ethoxy or imidazolyl. The reaction may be generally carried out in an aprotic solvent such as tetrahydrofurane, methylene chloride, chloroform, acetone, acetonitrile, benzene, toluene, ethylacetate, carbon tetrachloride or dimethylformamide, optionally in the presence of an acid acceptor, such as trietylamine, pyridine, sodium or potassium carbonate at a temperature between 0° C. and 100° C., preferably at room temperature.

Compounds of general formula V, used as starting materials in the above described process may be prepared by reducing a compound of general formula VII

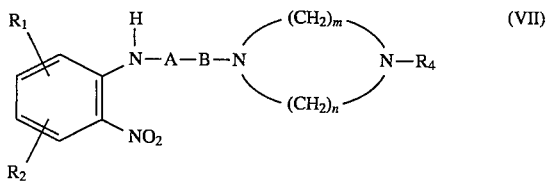

wherein $R_1$, $R_2$, $R_4$, A, B, m and n are as hereinbefore defined, with hydrogen or a hydrogen donor such as ammonium formate, cyclohexene, cyclohexadiene or hydrazine.

The reduction is preferably carried out with hydrogen in the presence of a suitable catalyst, preferably 5% or 10% Pd on charcoal or Raney nickel in the presence of a suitable solvent such as methanol, ethanol, toluene, water or a mixture of them. The reaction is preferably carried out at room pressure and temperature. The same reduction may be conveniently carried out with iron in acidic medium, for example hydrochloric acid, optionally in the presence of $FeCl_3$, or with Zn in acetic or hydrochloric acid, with $SnCl_2$ in hydrochloric acid or with other reducing agents such as titanium trichloride, ferrous sulphate, hydrogen sulphide or its salts, sodium hydrosulphide. When A is absent, the compounds of formula VII may be conveniently prepared by reacting a compound of general formula (VIII)

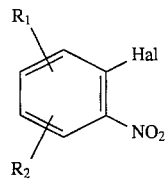

with a compound of general formula (IX)

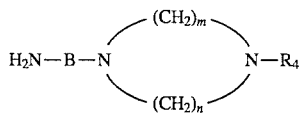

wherein $R_1$, $R_2$, $R_4$, B, m and n are as hereinbefore defined and Hal is a leaving group such as halogen, preferably chlorine. The reaction may be conveniently carried out with inert solvents such as butanol, isopropanol, ethanol and like or without solvents at a temperature between 50° C. and 200° C.

The compounds of general formula (IX) may be, in turn, conveniently prepared for example by reducing the corresponding nitrile of general formula (X)

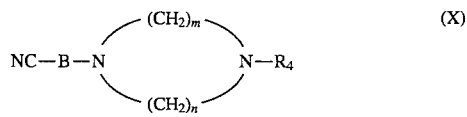

wherein $R_4$, m and n are as hereinbefore defined and B contains a carbon atom less in comparison with the above defined. The reaction may be conveniently carried by catalytic hydrogenation in the presence of ammonia or of acids, such as hydrochloric acid in the presence of a catalyst such as Ni-Raney, platinum dioxide and like. Alternatively the nitriles of general formula (X) may be reduced with metal hydride such as lithium aluminium hydride or with diborane.

When A represents a carbonyl group CO, the compounds of general formula (VII) may be prepared by reacting a compound of formula (XI)

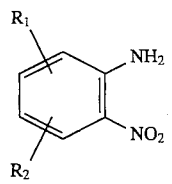

with a compound of formula (XII)

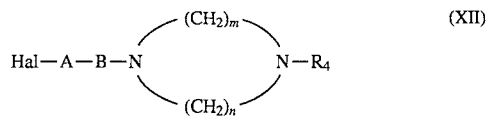

wherein $R_1$, $R_2$, $R_4$, B, m, n and Hal are as hereinbefore defined and A is carbonyl group. The reaction is carried out in an aprotic solvent such as tetrahydrofurane, acetonitrile, chloroform, toluene, chlorobenzene or without solvents and, optionally, in the presence of an acid acceptor, preferably in pyridine at a temperature between 20° C. and 100° C., preferably between 20° C. and 80° C. Compounds of formula (XII) may be prepared by known methods which are well known to anyone stilled in the art. When A represents a carboxyamidic group —CONH—, the compounds of general formula (VII) may be prepared by reacting a compound of general formula (XIII)

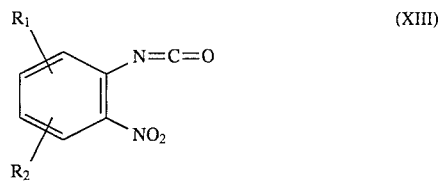

with a compound of formula (IX), wherein $R_1$ and $R_2$ are as above described. The reaction may be conveniently carried out in an aprotic solvent such as tetrahydrofurane, chloroform, toluene, benzene, cyclohexane at a temperature between 0° C. and 80° C., preferably between 5° C. and 30° C.; or c) when it is desired to prepare compounds of formula (I) wherein A is absent or it represents a carbonyl group, a compound of general formula (XIV)

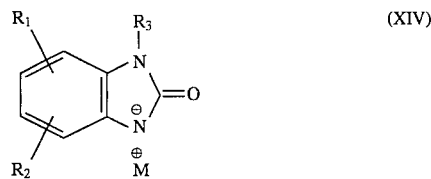

wherein $R_1$, $R_2$ and $R_3$ are as hereinbefore defined and M is a metal atom, such as sodium, potassium or lithium, preferably sodium, is reacted with a compound of formula XV

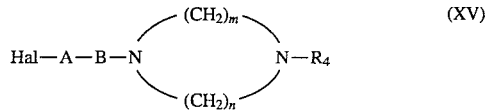

wherein Hal, B, m, n, A and $R_4$ are as above described. The reaction is preferably carried out in a polar aprotic solvent, such as dimethylformamide, tetrahydrofurane or pyridine at a temperature ranging from 0° C. to 100° C., preferably at room temperature.

Compound of formula XIV is generated "in situ" from the corresponding hydrogen compounds by means of sodium, potassium, sodium hydride, potassium hydride, potassium hydroxide, sodium hydroxide, potassium tert-butylate, butyllithium, lithium diisopropylamide, preferably sodium hydride; in case sodium or potassium hydroxide in aqueous concentrated solution are used, the reaction may be conveniently carried out in the presence of an inorganic insoluble solvent such as methylene chloride, in the presence of an phase transfer catalyst, such as a suitable ammonium quaternary salt at a temperature between 20° C. and 50° C.

Compounds of general formula (XV) wherein A is absent or represents a carbonyl group may be prepared from suitable starting compounds by methods which are well known to anyone stilled in the art, or d) when it is desired to prepare compounds of formula (I) wherein A is a —CONH— group, a compound of formula XVI

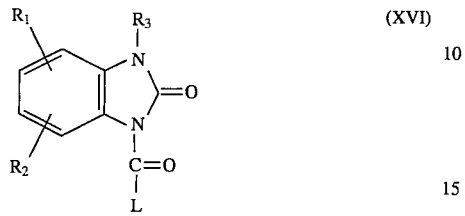

wherein $R_1$, $R_2$, and $R_3$ are as above defined, L represents a leaving group such as halogen or alkoxy, preferably chlorine, methoxy or ethoxy, is reacted with a compound of formula IX. The reaction is carried out in an inert aprotic solvent such as tetrahydrofurane, methylene chloride, ethyl acetate, acetonitrile, acetone, benzene, optionally in the presence of an organic or inorganic acid acceptor such as triethylamine, pyridine, sodium or potassium carbonate at a temperature ranging from −10° C. to the boiling point of the selected solvent, preferably at room temperature. Compounds of general formula XVI can be prepared with known methods from suitable starting compounds. Examples of compounds of general formula XVI may be found in EP 309,423, U.S. Pat. No. 4,061,861 and in J. Org. Chem. 38, 3498–502 (1973).

It has to be understood that compounds of general formula (I) containing an $R_1$, $R_2$, $R_3$ and $R_4$ group which may give rise to another $R_1$, $R_2$, $R_3$ and $R_4$ group, are useful novel intermediates. Some of these transformations may also occur in the intermediates for compounds of general formula (I).

Some examples of such conversions, which obviously are not exhaustive of all possibilities, are:

1) a nitro group may be transformed into an amino group by reduction.

2) an amino group may be transformed into a $C_{1-6}$ acylamino group by acylation with a suitable carboxylic acid derivative.

3) an amino group may be transformed into a $C_{1-4}$ alkyl N-mono or di-substituted group by alkylation.

4) an amino group may be transformed into a $C_{1-6}$ alkoxy carbonyl amino group by reaction with a suitable reactive $C_{1-6}$ alkyl carbonic acid monoester derivative.

5) a carboxyl group may be transformed into a $C_{1-6}$ alkoxy carbonyl group, or into a carbamoyl group optionally $C_{1-4}$ alkyl N-mono or di-substituted by reaction of a suitable reactive carboxylic acid derivative with appropriate alcohols and amines.

6) a carbamoyl group may be transformed into a cyano group by dehydration.

7) a $C_{1-6}$ alkyl thio or a $C_{1-6}$ alkyl sulphinyl group may be transformed into a $C_{1-6}$ alkyl sulphinyl or a $C_{1-6}$ alkylsulphonyl group by oxidation.

8) an aromatic hydrogen group may be transformed into a nitro group by nitration.

9) a hydrogen group may be transformed into a halogen group by halogenation.

10) A product of general formula I where $R_3$ is H, may be transformed in a product of formula I where $R_3$ is $C_{1-6}$ alkyl, $C_{2-6}$ alkenyl, $C_{2-6}$ alkynyl by alkylation with a suitable alkyl halide in the presence of a strong base such as sodium or potassium hydroxide, sodium or potassium hydride, potassium t-butilate in an aprotic solvent such as dimethylformamide or tetrahydrofurane at a temperature between 20° C. and 100° C. When aqueous concentrated solutions of sodium or potassium hydroxide are used, the reaction may be conveniently carried out in the presence of an unsoluble organic solvent, such as methylene chloride in the presence of phase transfer catalyst such as a suitable ammonium quaternary salt at a temperature between 20° C. and 50° C.

11) a tertiary amino group may be transformed into a quaternary ammonium derivative by reaction with a suitable alkylating agent such as methyl bromide or methyl iodide.

These transformations are well known to any expert of the branch.

The compounds of the general formula (I) prepared according to the above methods may optionally be converted by inorganic or organic acids into non-toxic, physiologically acceptable acid addition salts, for example by conventional methods such as by reacting the compounds as bases with a solution of the corresponding acid in a suitable solvent. Examples of non-toxic physiologically acceptable acid addition salts are those formed with hydrochloric, nitric, sulfuric, maleic, fumaric, citric, tartaric, methansulphonic, acetic, benzoic, succinic, gluconic, lactic, glycinic, malic, mucoic, glutammic, isethionic, phosphoric, ascorbic or sulphamic acid. Particularly preferred acids are hydrochloric, maleic and fumaric acid.

Particularly preferred compounds according to the present invention are:

1-[2-(4-(3-trifluoromethyl-phenyl)piperazin-1-yl)ethyl]-2,3-dihydro-1H-benzimidazol-2-one (Compound 3)

1-[4-(4-(3-chloro-phenyl)piperazin-1-yl)butyl]-2,3-dihydro-1H-benzimidazol-2-one (Compound 4)

1-[4-(4-(3-trifluoromethyl-phenyl)piperazin-1-yl)butyl]-2,3-dihydro-1H-benzimidazol-2-one (Compound 8)

1-[4-(4-(3-trifluoromethyl-phenyl)piperazin-1-yl)butyl]-3-methyl-2,3-dihydro-1H-benzimidazol-2-one (Compound 9)

1-[4-(4-(3-trifluoromethyl-phenyl)piperazin-1-yl)butyl]-3-isopropyl-2,3-dihydro-1H-benzimidazol-2-one (Compound 15)

1-[3-(4-(3-trifluoromethyl-phenyl)piperazin-1-yl)propyl]-2,3-dihydro-1H-benzimidazol-2-one (Compound 18)

6-methoxy-1-[4-(4-(3-trifluoromethyl-phenyl)piperazin-1-yl)butyl]-2,3-dihydro-1H-benzimidazol-2-one (Compound 25)

1-[4-(4-(1-naphtyl)piperazin-1-yl)butyl]-2,3-dihydro-1H-benzimidazol-2-one (Compound 30)

As already mentioned hereinbefore, the new compounds of formula (I) , according to the present invention, show interesting pharmacological properties owing to their activity on CNS serotonergic receptors, particularly 5-$HT_{1A}$ and 5-$HT_2$ receptor subtypes. Therefore the new compounds are commercially useful in the prevention and in the treatment of disorders wherein the alterated functionality of 5-$HT_{1A}$ and 5-$HT_2$ receptors, as above mentioned, is involved.

The biochemical and pharmacological profile of the compounds object of the present invention was assessed by evaluating their affinity for 5-$HT_{1A}$ and 5-$HT_2$ receptors and their efficacy was established: a) in inducing the well-known behavioural syndrome due to the stimulation of 5-$HT_{1A}$ receptors and b) by evaluating the antagonism towards the behavioural syndrome induced by quipazine stimulating the 5-HT$_2$ receptors.

Receptor Binding Studies

Receptor binding studies on 5-HT$_{1A}$ and 5-HT$_2$ receptors were carried out to determine the affinity of the test compounds.

5-HT$_{1A}$ RECEPTOR

Tissue preparation

Rats (male Sprague Dawley, 200–250 g) were used. The Hippocampi of these animals were homogenized in 10 volumes of ice cold TRIS buffer (pH 7.4). The homogenate was diluted 1:400 (w:v) in the same buffer to have a final protein concentration of about 200 µg/mL, filtered and incubated at 37° C. for 10 min, before use.

Binding assay

Displacement experiments were performed by incubating the homogenate (980 µL) in the presence of [$^3$H]-8OH-DPAT (1.0– 1,5 nM) (10 µL) and of different concentrations of the test compounds dissolved in the test buffer (10 µL), at 30° C. for 15 min (final volume: 1 mL).

Non specific binding was determined in the presence of 100 µM 5-HT (10 µL). The separation of [$^3$H]-8-OH-DPAT, free from that bound to the receptor, was carried out by the filtration technique (GF/B filters, Whatman). The radioactivity present was counted by liquid scintillation spectrometry.

Data analysis

The affinity values (Ki) for the compounds were obtained by a non linear least squares regression analysis on the basis of a one binding site model. The values were corrected on the basis of the radioligand occupancy on the receptors according to the equation: $Ki=IC_{50}/(1+[C]/K_D)$, where [C] and $K_D$ represent the concentration and the dissociation constant, respectively, of the radioligand used ([$^3$H]-8-OH-DPAT).

5-HT$_2$ RECEPTOR

Tissue preparation

Rats (male Sprague Dawley, 200–250 g) were used. Cerebral cortices were homogenized in 10 volumes of ice cold 0.32M sucrose. After the centrifugation of the homogenate (1,000×g for 10 min) the supernatant was then recentrifuged at 48,000×g for 15 min. The resulting pellet was resuspended in 10 volumes of 50 mM TRIS buffer (pH 7.4), incubated at 37° C. for 10 min and recentrifuged at 48,000×g for 15 min. The residue was then resuspended in 10 volumes of 50 mM TRIS buffer (pH 7.4).

Binding assay

The tissue was diluted 1:100 (w:v) in 50 mM TRIS buffer (pH 7.4) to have a final protein concentration of about 200 µg/mL.

Displacement experiments were performed by incubating the homogenate (980 µL) in the presence of [$^3$H]-Ketanserine (0.5–1.0 nM) (10 µL) and of different concentrations of the test compounds dissolved in the assay buffer (10 µL), at 37° C. for 10 min (final volume: 1 mL).

Non specific binding was determined in the presence of 100 µM Methysergide (10 µL). The separation of [$^3$H]-Ketanserine free from that bound to the receptor was carried by the filtration technique (GF/B filters, Whatman). The radioactivity present was counted by liquid scintillation spectrometry.

Data analysis

The affinity values (Ki) for the compounds were obtained by non linear least squares regression analysis on the basis of a one binding site model. These values were corrected on the basis of the radioligand occupancy on the receptors according to the equation: $Ki=IC_{50}/(1+[C]/K_D)$, where [C] and $K_D$ represent the concentration and the dissociation constant, respectively, of the radioligand used ([$^3$H]-Ketanserine).

The results of some of the compounds of the present invention on the affinity to the 5-HT$_{1A}$ and 5-HT$_2$ receptors are reported in Table 1.

TABLE 1

AFFINITY FOR 5-HT$_{1A}$ AND 5-HT$_2$ RECEPTORS

| Compound | Ki (nM) 5-HT$_{1A}$ | 5-HT$_2$ |
|---|---|---|
| 1 | 13 | 36 |
| 3 | 50 | 133 |
| 4 | 74 | 1.4 |
| 8 | 53 | 9.5 |
| 9 | 23 | 14 |
| 10 | 5 | 30 |
| 15 | 80 | 20 |
| 17 | 30 | 8 |
| 18 | 25 | 4 |
| 13 | 15 | 15 |
| 24 | 12 | 65 |
| 25 | 100 | 25 |
| 30 | 10 | 7 |

Animal Studies

Behavioral Syndrome

This syndrome, which relates to the stimulation of 5-HT$_{1A}$ receptors and has been described by Goodwin and Green (1985), consists in flat posture, forepaw treading and hindlimb abduction. A control animal does not show this behavioural pattern. The test consists of administering the compound and registering the presence of the above mentioned symptoms within 50 min giving them a score. The results are expressed as the sum of said scores for each rat (Tab. 2).

TABLE 2

INDUCTION OF 5-HT$_{1A}$ RELATED SYNDROME

| Compound | Dose mg/kg/ip | Total score |
|---|---|---|
| VEHICLE | — | 0 |
| 1 | 8 | 7.3 ± 0.9 |
| 3 | 16 | 5.3 ± 1.2 |
| 4 | 8 | 0.8 ± 0.5 |
|  | 16 | 3.3 ± 1.0 |
| 8 | 8 | 3.0 ± 2.7 |
| 9 | 8 | 2.0 ± 0.6 |
| 10 | 8 | 3.0 ± 0.4 |
| 17 | 8 | 1.5 ± 0.7 |
|  | 32 | 10.3 ± 2.9 |
| 18 | 16 | 3.8 ± 2.2 |
|  | 32 | 12.0 ± 3.2 |
| 13 | 32 | 3.8 ± 1.3 |
| 24 | 8 | 4.3 ± 1.1 |
| 25 | 8 | 2.0 ± 1.2 |

Values represent mean± s.e. from 4 rats

Antagonism of Quipazine-induced head twitches

Head twitches depend on the stimulation of 5-HT$_2$ receptors (Goodwin an Green (1985)).The test consists of administering the compound in quipazine-treated animals and scoring the number of head twitches within 20 minutes (Table 3).

TABLE 3

| DOSE OF COMPOUND (ID$_{50}$) WHICH ANTAGONIZES THE SYNDROME INDUCED BY QUIPAZINE | |
| --- | --- |
| Compound | ID50 µg/kg/ip |
| 1 | 720 |
| 3 | 498 |
| 4 | 250 |
| 8 | 385 |
| 9 | 1720 |
| 10 | 3300 |
| 17 | 178 |
| 18 | 170 |
| 13 | 8200 |
| 24 | 102 |
| 25 | 1420 |

According to a further feature of the present invention there are provided pharmaceutical compositions comprising as active ingredient at least one compound of formula (I), as hereinbefore defined, or a physiologically acceptable acid addition salt thereof in association with one or more pharmaceutical carriers, diluents or excipients. For pharmaceutical administration the compounds of general formula (I) and their physiologically acceptable acid addition salts may be incorporated into the conventional pharmaceutical preparations in solid, liquid or spray form. The compositions may, for example, be presented in a form suitable for oral, rectal, parenteral administration or for nasal inhalation. Preferred forms include, for example, capsules, tablets, coated tablets, ampoules, suppositories and nasal spray.

The active ingredient may be incorporated in excipients or carriers conventionally used in pharmaceutical compositions such as, for example, talc, arabic gum, lactose, gelatine, magnesium stearate, corn starch, aqueous or non-aqueous vehicles, polyvinylpirrolidone, semisynthetic gliceride of fatty acids, benzalcon chloride, sodium phosphate, EDTA, polysorbate 80.

In order to increase the solubility of the compounds of general formula (I) or their physiological acceptable salts, surfactants, non-ionic surfactants such as PEG 400, cyclodextrins, metastable polymorphs, inert absorbents such as bentonite may be incorporate. Furthermore some techniques may be employed by preparing for example eutectic mixtures and/or solid dispersions by using mannitol, sorbitol, saccharose, succinic acid, or physical modified forms by using hydrosoluble polymers, PVP, PEG 4000–20000.

The compositions are advantageously formulated in dosage units, each dosage unit being adapted to supply a single dose of the active ingredient. Each dosage unit may conveniently contain from 0,01 mg to 100 mg and preferably from 0,1 mg to 50 mg.

The following examples illustrate the preparation of some new compounds according to the present invention and will enable other skilled in the art to understand it more completely. It should be understood, however, that the invention is not limited solely to the particular examples given below.

Description 1

1-(6-Chlorohexyl)-2,3-dihydro-1H-benzimidazol-2-one

The above mentioned compound was prepared analogously to the procedure described in J. Het. Chem. 18, 85 (1981) from 1-( -phenylvinyl)-2,3-dihydro-1H-benzimidazol-2-one and 1,6-dichloro hexane. The protecting group was then removed by acid hydrolysis with hydrochloric acid following the above procedure. M.p. 80°–84° C.

Analogously were prepared:
1-(2-Chloroethyl)-2,3-dihydro-1H-benzimidazol-2-one
M.p. 146°–148° C.

1-(3-Chloropropyl)-2,3-dihydro-1H-benzimidazol-2-one
M.p. 113°–115° C.

1-(4-Chlorobutyl)-2,3-dihydro-1H-benzimidazol-2-one
M.p. 80°–81° C.

Description 2

1-(α-phenylvinyl)-3-n-hexyl-2,3-dihydro-1H-benzimidazol-2-one

The above mentioned compound was prepared similarly to the procedure described in J. Het. Chem. 18, 85 (1981) for the preparation of the analogues bearing in position 1 a methyl, ethyl, allyl and isopropyl residue. The compound may be obtained from 1-(α-phenylvinyl)-2,3-dihydro-1H-benzimidazol-2-one and 1-bromohexane. The compound was used as such without further purification.

Description 3

1-n-hexyl-2,3-dihydro-1H-benzimidazol-2-one

The compound was prepared similarly to the procedure described in J. Het. Chem. 18, 85 (1981) for the preparation of the analogues bearing in position 3 a methyl, ethyl, allyl and isopropyl residue. The compound may be obtained from 1-(α-phenylvinyl)-3-n-hexyl-2,3-dihydro-1H-benzimidazol-2-one by acid hydrolysis with hydrochloric acid. The compound was used as such without further purification.

Description 4

1-(4-Chlorobutyl)-3-n-hexyl-2,3-dihydro-1H-benzimidazol-2-one

The compound may be prepared according to the procedure described in J. Het. Chem. 18, 85 (1981) from 3-n-hexyl-2,3-dihydro-1H-benzimidazol-2-one and 1,4-dichlorobutane.

Analogously may be prepared:
1-(4-Chlorobutyl)-3-methyl-2,3-dihydro-1H-benzimidazol-2-one
1-(4-Chlorobutyl)-3-isopropyl-2,3-dihydro-1H-benzinidazol-2-one
1-(4-Chlorobutyl)-3-allyl-2,3-dihydro-1H-benzimidazol-2-one
1-(6-Chlorohexyl)-3-ethyl-2,3-dihydro-1H-benzimidazol-2-one All the above mentioned compounds were used as such without further purification.

Description 5

N-(2-Amino-4-methoxyphenyl)-ethyl carbamate

A solution of N-(2-nitro-4-methoxyphenyl)-ethyl carbamate (4 g) (prepared by allowing 4-methoxy-2-nitroaniline to react with ethylchloroformate in pyridine at reflux for 4 hrs, m.p. 56°–59° C.) in absolute ethanol (150 ml) was hydrogenated at room pressure and temperature in the presence of 10% palladium on charcoal (0,2 g). After absorption of the calculated amount of hydrogen was over, the catalyst was filtered on celite and the alcoholic solution was evaporated. The desired compound (3,8 g) was obtained as a solid. M.p. 74°–76° C.

Description 6

5-Methoxy-2,3-dihydro-2-oxo-1H-benzimidazol-1-ethyl carboxylate

A solution of N-(2-amino-4-methoxyphenyl)ethyl carbamate (0,5 g) and triethylamine (0,4 ml) in $CH_2Cl_2$ (10 ml), was dropped into a solution of trichloromethylchloroformate (0,32 ml) in $CH_2Cl_2$ (5 ml) under stirring at 5° C. When the addition was over, the reaction was allowed to reach room temperature and stirring was continued for 1 hour. Water was then added and the product was extracted with $CH_2Cl_2$. After evaporation of the solvent the solid residue was purified by washing with diethyl ether. 0,2 g of the desired product was obtained. M.p. 176°–178° C.

Description 7

5-Methoxy-3-(2-bromoethyl)-2,3-dihydro-2-oxo-1H-benzimidazol-1-ethyl carboxylate

To a suspension of 80% sodium hydride (0,38 g) in anhydrous dimethylformamide (45 ml) 5-methoxy-2,3-dihydro-2-oxo-1H-benzimidazol-1-ethyl carboxylate (3 g) was added portionwise. After the mixture was stirred for 1 hour at room temperature, a solution of 1,2-dibromoethane (1,1 ml) in 6 ml of dimethylformamide was added. Stirring was kept on 12 hours at room temperature. The water was then added and the product which separated was collected by filtration. The raw solid was purified by chromatography on Silicagel; eluent $CH_2Cl_2$/MeOH/32% $NH_4OH$ 98:2:02. 1,0 g of the desired product were obtained. M.p. 118°–120° C.

Similarly, starting from 1,4-dibromobutane, 5-methoxy-3-(4-bromobutyl)-2,3-dihydro-2-oxo-1H-benzimidazole-1-ethylcarboxylate may be prepared.

Description 8

1-(3-Trifluoromethylphenyl)-hexahydro-1,4-diazepine i) Tri -(3-trifluoromethylphenyl)bismuth

3-Trifluoromethylbromobenzene (3.1 ml) dissolved in dry diethyl ether (100 ml) was cautiously added in 60 min to a suspension of magnesium (0.6 g) in the same solvent (5 ml), to which a small crystal of iodine was previously added. The formation of the Grignard reagent was induced by local heating and, once started, the reaction was continued at reflux for further 60 min.

After cooling to 0° C., previously dryed bismuth trichloride (3,5 g) was added portionwise and then reflux and stirring was continued for 3 hrs. Water was then added and the intermediate tri-(3-trifluoromethylphenyl)bismuth was extracted into ethyl acetate. After drying, evaporation of the solvent under vacuum, left 3,9 g of the desired compound as an oil. The compound was further purified by column chromatography on Silicagel using hexane/ethylacetate 95:5 as the eluent. Yield 2,46 g. Yellow oil. MS (C.I.): [M+H]$^+$ 645, 625, 498, 353 m/z.

ii) 1-(3-Trifluoromethylphenyl) piperidin-4-one

Piperidin-4-one monohydrochloride, monohydrate (3.0 g) was dissolved in water (15 ml) and 10% sodium hydroxide (8 ml) was added. The free base was extracted four times into methylene dichloride (150 ml); after separation of the layers, the organic phase was dessicated over $MgSO_4$.

In another flask, tri-(3-trifluoromethylphenyl) bismuth (6 g) was dissolved in dry methylenedichloride (70 ml), and copper acetate (1.55 g) was added. The previously prepared solution of piperidin-4-one was then added dropwise under stirring at room temperature and under a nitrogen stream. The reaction mixture became light blue and then turned green. Stirring was kept on for 2 days, then water was added. The insoluble material that separated was filtered off, the organic layer was separated, dessicated over $MgSO_4$ concentrated to dryness under vacuum. After chromatographic purification on Silicagel with eluent hexane/ethylacetate 80:20, 1.26 g of the desired compound were obtained. MS(C.I.): [M+H]$^+$ 244, 224 m/z.

iii) 1-(3-Trifluoromethylphenyl)hexahydro-1,4-diazepin-5-one 1-(3-trifluoromethylphenyl)piperidin-4-one (0.4 g) was dissolved into a mixture of glacial acetic (2.5 ml) and concentrated sulphuric acid (1.5 ml). The reaction mixture was cooled to 0° C. and sodium azide (118 mg) was added portionwise in eight hours. Stirring was continued overnight and then solid sodium hydroxyde in pellets was added under external cooling until pH 8–10 was reached. A small amount of water was also added. The desired compound was extracted into chloroform, the organic phase was dessicated over magnesium sulphate and evaporation of the solvent left 0.36 g of a white solid. M.p. 114°–115° C. MS (C.I.): [M+H]$^+$ 259, 239 m/z.

iiii) 1-(3-Trifluoromethylphenyl)hexahydro-1,4-diazepine

A solution of 1-(3-trifluoromethylphenyl)-hexahydro-1,4-diazepin-5-one (0.36 g) in anhydrous tetrahydrofurane was added dropwise to a suspension of $LiAlH_4$ (0.11 g) in the same solvent (10 ml) at room temperature under stirring. Stirring was continued for 3 hrs at room temperature and 4 hrs at reflux. After cooling, water was cautiously added and then the reaction mixture was filtered; the solvent was removed under vacuum and the compound was purified by column chromatography. Yield 0,11 g. Oil. MS (C.I.): [M+H]$^+$ 245, 225 m/z.

Description 9

7-Methoxy-1-naphtylpiperazine was prepared according to J. Med. Chem. 32, 1921–26 (1989).

Example 1

1-[4-(4-(2-methoxy-phenyl)piperazin-1-yl)butyl]-2,3-dihydro-1H-benzimidazol-2-one

(Compound 1)

A mixture of 1-(4-chlorobutyl)-2,3-dihydro-1H-benzimidazol-2-one (2 g) and of 1-(2-methoxyphenyl)piperazine hydrochloride (2,03 g) with sodium carbonate (1,88 g) and potassium iodide (0,01 g) in absolute ethanol (100 ml) was refluxed for 18 hours. After filtering the inorganic salts and evaporating the solvent the residue was dissolved in diluted HCl and washed with ethyl acetate. The aqueous phase was made strongly alkaline with 30% NaOH and the product, which separated, was extracted into ethyl acetate. After drying, the solvent was removed under vacuum, and a white solid was obtained; it was treated with diethylether, filtered and recrystallized from isopropanol. 2,1 g of the desired compound were obtained. M.p. 160°–161° C.

Analysis $C_{22}H_{28}N_4O_2$ Found % C 69,00 H 7,44 N 14,15 Calc. % C 69,45 H 7,42 N 14,73 $^1$H NMR (CDCl$_3$) 9.82 (s, 1H), 7.1–6.7 (8H), 3.93 (t, 2H), 3.84 (s, 3H), 3.1–2.9 (4H), 2.8–2.5 (4H), 2.45 (t, 2H), 1.9–1.4 (4H)

Following the above described process and using the appropriate benzimidazol-2-one derivatives and arylpiperazine the following may be prepared:

1-[4-(3-(3-chlorophenyl)piperazin-1-yl)propyl]-2,3-dihydro-1H-benzimidazol-2-one (Compound 2)

Dihydrochloride salt (isopropanol) M.p. 165°–170° C.

Analysis $C_{20}H_{23}ClN_4O$ . 2HCl Found % C 53,48 H 5,71 N 12,39 Calc. % C 54,13 H 5,68 N 12,62 $^1$H NMR (DMSO-d$_6$/CDCl$_3$ 5:2) 11.09 (b, 1H), 10.81 (s, 1H), 7.3–6.7 (8H), 4.71 (s, 1H+HDO), 3.94 (t, 2H), 4.1–3.0 (10H), 2.26 (m, 2H)

1-[2-(4-(3-trifluoromethyl-phenyl)piperazin-1-yl)ethyl]-2,3-dihydro-1H-benzimidazol-2-one (Compound 3)

Hydrochloride salt (isopropanol) M.p. 230°–231° C.

Analysis $C_{20}H_{21}F_3N_4$ O . HCl Found % C 56,37 H 5,20 N 13,12 Calc. % C 56,27 H 5,20 N 13,13 $^1$H NMR (DMSO-d$_6$/CDCL$_3$ 5:2) 11.09 (b, 1H), 11.04 (s, 1H), 7.5–6.9 (5H), 4.36 (t, 2H), 4.1–3.1 (10H)

1-[4-(4-(3-chlorophenyl)piperazin-1-yl)butyl]-2,3-dihydro-1H-benzimidazol-2-one (Compound 4)

Hydrochloride salt (isopropanol) M.p. 217°–220° C.

Analysis $C_{21}H_{25}ClN_4O$ . 2HCl Found % C 54,87 H 5,87 N 12,34 Calc. % C 55,09 H 5,94 N 12,24 $^1$H NMR (DMSO-d$_6$/CDCL$_3$ 5:2) 11.01 (b, 1H), 10.92 (s, 1H), 7.3–6.8 (8H), 4.42 (b, 1H), 4.0–3.8 (4H), 3.50 ( d, 2H), 3.3–3.0 (6H), 1.9–1.6 (4H)

1-[4-(4-(pyrimidin-2-yl)piperazin-1-yl)butyl]-2,3-dihydro-1H-benzimidazol-2-one (Compound 5)

Hydrochloride salt (isopropanol) M.p. 237°–242° C.

Analysis $C_{19}H_{24}N_6O$ . 2HCl Found % C 53,47 H 6,34 N 19,51 Calc. % C 53,65 H 6,16 N 19,76 $^1$H NMR (CDCL$_3$) 9.75 ( s, 1H), 8.29 (d, 2H), 7.2–6.9 (4H), 6.47 (m, 1H), 4.1–3.7 (6H) 2.7–2.4 (6H), 2.1–1.5 (4H). The spectrum was recorded on the compound in the form of free base.

1-[2-(4-(3-chlorophenyl)piperazin-1-yl)ethyl]-2,3-dihydro-1H-benzimidazol-2-one (Compound 6)

Hydrochloride salt (isopropanol) M.p. 230°–231° C.

Analysis $C_{19}H_{21}ClN_4O$ . 2HCl Found % C 53,39 H 5,64 N 13,06 Calc. % C 53,10 H 5,39 N 13,04 $^1$H NMR (DMSO-d$_6$) 11.10 (b, 2H), 7.35 (m, 1H), 7.26 (m, 1H), 7.1–7.0 (4H), 6.97 (d, 1H), 6.87 (d, 2H), 4.32 (t, 2H), 4.1–3.0 (10H)

1-[2-(4-(2-methoxyphenyl)piperazin-1-yl)ethyl]-2,3-dihydro-1H-benzimidazol-2-one (Compound 7)

Hydrochloride salt (isopropanol) M.p. 241°–242° C.

Analysis $C_{20}H_{24}N_4O_2$ . 2HCl Found % C 56,00 H 6,24 N 12,79 Calc. % C 56,47 H 6,16 N 13,17 $^1$H NMR (DMSO-d$_6$/CDCL$_3$ 5:2) 11.0 (b, 1H), 10.97 (s, 1H), 7.4–6.7 (9H), 4.35 (t, 2H), 3.82 (s, 3H), 4.0–2.9 (10H)

1-[4-(4-(3-trifluoromethyl-phenyl)piperazin-1-yl)butyl]-2,3-dihydro-1H -benzimidazol-2-one (Compound 8)

M.p. 114°–115° C.

Analysis $C_{22}H_{25}F_3N_4O$ Found % C 62,99 H 6,18 N 13,41 Calc. % C 63,15 H 6,02 N 13,39 $^1$H NMR (CDCL$_3$) 10.16 (s, 1H), 7.34 (m, 1H), 7.2–7.0 (7H), 3.94 (t, 2H), 3.30 (m, 4H), 2.74 (m, 4H), 2.61 (t, 2H), 2.0–1.6 (4H)

1-[4-(4-(3-trifluoromethyl-phenyl)piperazin-1-yl)butyl]-3-methyl-2,3-dihydro-1H-benzimidazol-2-one (Compound 9)

Hydrochloride salt (isopropanol) M.p. 215°–216° C.

Analysis $C_{23}H_{27}F_3N_4O$ . HCl Found % C 59,19 H 6,20 N 12,14 Calc. % C 58,91 H 6,02 N 11,95 $^1$H NMR (DMSO-d$_6$/CDCL$_3$ 5:2) 10.81 (b, 1H), 7.5–6.9 (8H), 3.90 (t, 2H), 3.36 (s, 3H), 4.1–3.0 (10H), 2.0–1.6 (4H)

1-[3-(4-(2-methoxyphenyl)piperazin-1-yl)propyl]-2,3-dihydro-1H-benzimidazol-2-one (Compound 10)

Hydrochloride salt (isopropanol) M.p. 200°–204° C.

Analysis $C_{21}H_{26}N_4O_2$ . 2HCl Found % C 56,93 H 6,50 N 12,57 Calc. % C 57,41 H 6,42 N 12,75 $^1$H NMR (DMSO-d$_6$/CDCL$_3$ 5:2) 11.12 (b, 1H), 10.87 (s, 1H), 7.3–6.9 (8H), 6.75 (s, 1H+HDO), 3.92 (t, 2H), 3.81 (s, 3H), 3.8–3.1 (10H), 2.19 (m, 2H)

1-[4-(4-phenyl-piperazin-1-yl)butyl]2,3-dihydro-1H-benzimidazol-2-one (Compound 11)

Hydrochloride salt (isopropanol) M.p. 255°–259° C.

Analysis $C_{21}H_{26}N_4O$ . 2HCl Found % C 59,32 H 6,69 N 12,99 Calc. % C 59,57 H 6,67 N 13,23 $^1$H NMR (DMSO-d$_6$/CDCL$_3$ 5:2) 11.11 (b, 1H), 10.82 (s, 1H), 9.10 (s, 1H+HDO), 7.4–6.7 (9H), 4.0–3.1 (12H), 1.9–1.7 (4H)

1-[6-(4-(3-trifluoromethyl-phenyl)piperazin-1-yl)hexyl]-2,3-dihydro-1H-benzimidazol-2-one (Compound 12)

Hydrochloride salt (isopropanol) M.p. 118°–120° C.

Analysis $C_{24}H_{29}F_3N_4O \cdot HCl$ Found % C 57,21 H 6,28 N 11,00 . $H_2O$ Calc. % C 55,54 H 6,44 N 11,18 $^1H$ NMR (DMSO-$d_6$/CDCL$_3$ 5:2) 10.89 (b, 1H), 10.76 (s, 1H), 7.6–6.9 (8H), 4.1–3.0 (12H), 2.0–1.2 (8H)

1-[6-(4-(3-trifluoromethyl-phenyl)piperazin-1-yl)hexyl]-3-ethyl-2,3-dihydro-1H-benzimidazol-2-one (Compound 13)

Hydrochloride salt (isopropanol) M.p. 138°–139° C.

Analysis $C_{26}H_{33}F_3N_4O \cdot HCl$ Found % C 61,21 H 6,64 N 10,67 Calc. % C 61,11 H 6,71 N 10,96 $^1H$ NMR (CDCL$_3$) 12.91 (b, 1H), 7.4–6.8 (5H), 4.1–2.8 (14H), 1.33 (t, 3H), 2.2–1.2 (8H)

1-[4-(4-(2-methoxyphenyl)piperazin-1-yl)butyl]-3-allyl-2,3-dihydro-1H-benzimidazol-2-one (Compound 14)

Hydrochloride salt (isopropanol) M.p. 201°–204° C.

Analysis $C_{25}H_{32}N_4O_2 \cdot 2HCl$ Found % C 61,35 H 7,09 N 11,18 Calc. % C 60,85 H 6,94 N 11,35 $^1H$ NMR (DMSO-$d_6$/CDCL$_3$ 5:2) 11.07 (b, 1H), 8.04 (s, 1H+HDO), 7.2–6.8 (8H), 5.90 (m, 1H), 5.2–5.0 (2H), 4.48 (d, 2H), 3.92 (t, 2H), 3.82 (s, 3H), 3.7–3.0 (10H), 2.0–1.7 (4H)

1-[4-(4-(3-trifluoromethyl-phenyl)piperazin-1-yl)butyl]-3-isopropyl-2,3-dihydro-1H-benzimidazol-2-one (Compound 15)

Hydrochloride salt (isopropanol) M.p. 181°–184° C.

Analysis $C_{25}H_{31}F_3N_4O \cdot HCl$ Found % C 60,01 H 6,51 N 11,24 Calc. % C 60,42 H 6,49 N 11,27 $^1H$ NMR (CDCL$_3$) 12.85 (b, 1H), 7.4–6.9 (8H), 4.70 (m, 1H), 3.92 (t, 2H), 4.0–2.8 (10H), 2.2–1.8 (4H), 1.53 (d, 6H)

1-[4-(4-(3-chlorophenyl)piperazin-1-yl)butyl]-3-n-hexyl-2,3-dihydro-1H-benzimidazol-2-one (Compound 16)

Hydrochloride salt (isopropanol) M.p. 107°–111° C.

Analysis $C_{27}H_{37}ClN_4O \cdot HCl$ Found % C 64,57 H 7,53 N 11,10 Calc. % C 64,15 H 7,58 N 11,08 $^1H$ NMR (CDCL$_3$) 12.80 (b, 1H), 7.2–6.5 (8H), 3.9–2.7 (14H), 2.3–1.2 (12H), 0.87 (m, 3H)

1-[4-(4-(3-chlorophenyl)piperazin-1-yl)butyl]-3-methyl-2,3-dihydro-1H-benzimidazol-2-one (Compound 17)

Hydrochloride salt (isopropanol) M.p. 214°–216° C.

Analysis $C_{22}H_{27}ClN_4O \cdot HCl$ Found % C 60,88 H 6,58 N 12,86 Calc. % C 60,69 H 6,48 N 12,87 $^1H$ NMR (CDCL$_3$) 12.84 (b, 1H), 7.3–6.7 (8H), 3.93 (t, 2H), 3.42 (s, 3H), 4.0–2.9 (10H), 2.1–1.8 (4H)

1-[3-(4-(3-trifluoromethyl-phenyl)piperazin-1-yl)propyl]-2,3-dihydro-1H-benzimidazol-2-one (Compound 18)

Hydrochloride salt (isopropanol) M.p. 160°–162° C.

Analysis $C_{21}H_{23}F_3N_4O \cdot 2HCl$ Found % C 52,84 H 5,29 N 11,77 Calc. % C 52,84 H 5,28 N 11,74 $^1H$ NMR (DMSO-$d_6$/CDCL$_3$ 5:2) 11.14 (b, 1H), 10.87 (s, 1H), 7.6–6.9 (8H), 6.64 (s, 1H+HDO), 3.93 (t, 2H), 4.1–3.0 (10H), 2.21 (m, 2H)

1-[4-(4-(2-chlorophenyl)piperazin-1-yl)butyl]-2,3-dihydro-1H-benzimidazol-2-one (Compound 19)

Hydrochloride salt (ethanol) M.p. 247°–250° C.

Analysis $C_{21}H_{25}ClN_4O \cdot HCl$ Found % C 59,36 H 6,34 N 12,96 Calc. % C 59,86 H 6,22 N 13,30 $^1H$ NMR (DMSO-$d_6$/CDCL$_3$ 5:2) 10.81 (b, 1H), 10.80 (s, 1H), 7.4–6.9 (8H), 3.86 (t, 2H), 3.7–3.1 (10H), 2.0–1.7 (4H)

1-[4-(4-(3-methoxyphenyl)piperazin-1-yl)butyl]-2,3-dihydro-1H-benzimidazol-2-one (Compound 20)

Hydrochloride salt (ethanol) M.p. 190°–192° C.

Analysis $C_{22}H_{28}N_4O_2 \cdot 2HCl$ Found % C 58,36 H 6,69 N 12,38 Calc. % C 58,28 H 6,67 N 12,36 $^1H$ NMR (DMSO-$d_6$/CDCL$_3$ 5:2) 11.05 (b, 1H), 10.80 (s, 1H), 7.3–7.0 (5H), 6.6–6.4 (3H), 5.40 (s, 1H +HDO), 3.74 (s, 3H), 4.0–3.0 (12H), 2.0–1.6 (4H)

1-[4-(2-(7-methoxynapht-1-yl)piperazin-1-yl)ethyl]-2,3-dihydro-1H-benzimidazol-2-one (Compound 22)

Hydrochloride salt (ethanol) M.p. 240°–242° C.

Analysis $C_{24}H_{26}N_4O_2 \cdot HCl$ Found % C 65,49 H 6,31 N 12,58 Calc. % C 65,67 H 6,20 N 12,76 $^1H$ NMR (DMSO-$d_6$/CDCL$_3$ 5:2) 10.97 (s, 1H), 10.63 (b, 1H), 7.9–7.0 (10H), 4.37 (t, 2H), 3.94 ( s, 3H), 4.1–3.2 (10H)

1-[4-(4-(5-benzodioxan-piperazin-1-yl)butyl]-2,3-dihydro-1H-benzinidazol-2-one (Compound 29)

Hydrochloride salt (isopropanol) M.p. 186°–188° C.

Analysis $C_{23}H_{28}N_4O_3 \cdot 2HCl$ Found % C 56,96 H 6,57 N 11,83 Calc. % C 57,38 H 6,28 N 11,64 $^1H$ NMR (DMSO-$d_6$) 10.93 (s, 1H), 10.9 (b, 1H), 7.15 (m, 1H), 7.1–6.9 (3H), 6.76 (m, 1H), 6.6–6.5 (2H), 4.53 (s, 1H+HDO), 4.24 (s, 4H), 3.83 (t, 2H), 3.6–3.4 (4H), 3.3–3.0 (6H), 1.9–1.6 (4H)

1-[4-(4-(1-naphtyl)piperazin-1-yl)butyl]-2,3-dihydro-1H-benzimidazol-2-one (Compound 30)

Hydrochloride salt (isopropanol) M.p. 264°–267° C.

Analysis $C_{25}H_{28}N_4O \cdot 2HCl$ Found % C 63,66 H 6,59 N 11,99 Calc. % C 63,42 H 6,39 N 11,83 $^1H$ NMR (DMSO-$d_6$) 10.86 (s, 1H), 10.51 (b, 1H), 8.12 (m, 1H), 7.89 (m, 1H), 7.64 (d, 1H), 7.6–7.5 (2H), 7.42 (d, 1H), 7.2–7.0 (5H), 3.89 (t, 2H), 3.7–3.2 (10H), 2.0–1.7 (4H)

1-[2-(4-(3-trifluoromethyl-phenyl)hexahydro-1H-1,4-
diazepin-1-yl)ethyl]-2,3-dihydro-1H-
benzimidazol-2-one (Compound 31)

Hydrochloride salt (Ethylacetate - diethyl ether) M.p. 128°–130° C.

Analysis $C_{21}H_{23}F_3N_4O$ . HCl Found % C 55,81 H 5,56 N 12,19 Calc. % C 57,21 H 5,49 N 12,71 $^1$H NMR (CDCL$_3$) 12.77 (b, 1H), 9.86 (b, 1H), 7.5–6.8 (8H), 4.44 (b, 2H), 4.2–2.0 (10H), 2.40 (m, 2H)

1-[2-(4-phenyl-piperazin-1-yl)ethyl]-2,3-dihydro-1H-
benzimidazol-2-one (Compound 35)

Hydrochloride salt (isopropanol - ethanol) M.p. 232°–234° C.

Analysis $C_{19}H_{22}N_4O$ . HCl Found % C 62,84 H 6,46 N 15,43 Calc. % C 63,59 H 6.46 N 15,61 $^1$H NMR (DMSO-d$_6$/CDCL$_3$ 5:2) 11.0 (b, 1H), 10.97 (s, 1H), 7.4–6.7 (9H), 4.34 (t, 2H), 4.0–3.1 (10H)

1-[3-(3-phenylimidazolidin-1-yl)butyl]-2,3
-dihydro-1H-benzimidazol-2-one (Compound 36)

Example 2

6-methoxy-1-[2-(4-(3-trifluoromethyl-
phenyl)piperazin-1-yl)ethyl]-2,3-dihydro-1H-
benzimidazol-2-one (Compound 23)

5-Methoxy-3-(2-bromoethyl)-2,3-dihydro-2-oxo-1H-benzimidazol-1-ethyl carboxylate (0.6 g) was suspended into a mixture of ethanol (60 ml) and dry dimethylformamide (20 ml), in the presence of sodium carbonate (0.23 g). 3-Trifluoromethylphenylpiperazine (0,33 ml) was added dropwise to the suspension at room temperature under stirring, then the reaction mixture was heated to reflux for 14 hrs. The solvents were removed under vacuum and the raw material was purified by column chromatography on Silicagel; eluent methylenedichloride/methanol/32% ammonium hydroxide 98:2:0,2. The title compound was further purified by crystallization from 50% aqueous ethanol. Yield 0.1 g. The hydrochloride was obtained by adding the stoichiometric amount of aqueous hydrochloric acid and freeze-drying. Hydrochloride salt (water) M.p. 208°–210° C.

Analysis $C_{21}H_{23}F_3N_4O_2$ . HCl Found % C 55,28 H 5,22 N 11,85 Calc. % C 55,21 H 5,29 N 12,26 $^1$H NMR (DMSO-d$_6$/CDCL$_3$ 5:2) 11.09 (b, 1H), 10.75 (s, 1H), 7.5–6.8 (6H), 6.57 (m, 1H), 4.31 (t, 2H), 3.79 (s, 3H), 4.1–3.0 (10H)

Similarly were prepared:

6-methoxy-1-[4-(4-(2-methoxyphenyl)piperazin-1-
yl)butyl]-2,3-dihydro-1H-benzimidazol-2-one (Compound 24)

Hydrochloride salt (ethanol) M.p. 163°–165° C.

Analysis $C_{23}H_{30}N_4O_3$ . HCl Found % C 61,55 H 6,81 N 12,70 Calc. % C 61,80 H 6,99 N 12,53 $^1$H NMR (DMSO-d$_6$/CDCL$_3$ 5:2) 10.96 (b, 1H), 10.61 (s, 1H), 7.2–6.6 (6H), 6.53 (m, 1H), 3.81 (s, 3H), 3.77 (s, 3H), 3.9–3.0 (12H), 1.9–1.6 (4H)

6-methoxy
-1-[4-(4-(3-trifluoromethyl-phenyl)piperazin-1-
yl)butyl]-2,3-dihydro-1H-benzimidazol-2-one (Compound 25)

Hydrochloride salt (ethanol) M.p. 122°–124° C.

Analysis $C_{23}H_{27}F_3N_4O_2$ . HCl Found % C 56,79 H 5,74 N 11,38 Calc. % C 56,97 H 5,82 N 11,55 $^1$H NMR (DMSO-d$_6$/CDCL$_3$ 5:2) 11.04 (b, 1H), 10.59 (s, 1H), 7.5–6.7 (6H), 6.53 (m, 1H), 3.77 (s, 3H), 4.1–3.0 (12H), 2.0–1.6 (4H)

Description 10

4-(2-methoxyphenyl)-N-(2-nitro-5-chlorophenyl)-1-
piperazinbutanamine

The compound was prepared according to the method described in Farmaco Ed. Sci. 36, 359 (1981) from 2,4-dichloronitrobenzene and 4-(2-methoxyphenyl)-1-piperazinbutanamine. M.p. 227°–229° C. as hydrochloride salt.

Analogously may be prepared:
4-(2-methoxyphenyl)-N-(2-nitro-4,5-dichlorophenyl)-1-piperazinbutanamine. Oil
4-(2-methoxyphenyl)-N-(2-nitro-5-methylphenyl)-1-piperazinbutanamine hydrochloride salt. M.p. 227° C.
4-(2-methoxyphenyl)-N-(2-nitrophenyl)-1-piperazinbutanamine Description 11

4-(2-methoxyphenyl)-N-(2-amino-5-chlorophenyl)-1-
piperazinbutanamine

The compound was prepared according to the method described in Farmaco Ed. Sci. 36, 359 (1981) reducing 4-(2-methoxyphenyl)-N-(2-nitro-5-chlorophenyl)-1-piperazinbutanamine by catalytic hydrogenation. Oil.

Analogously may be prepared:
4-(2-methoxyphenyl)-N-(2-amino-5-methylphenyl)-1-piperazinbutanamine, hydrochloride salt. M.p. 233°–235° C.
4-(2-methoxyphenyl)-N-(2-amino-4,5-dichlorophenyl)-1-piperazinbutanamine. Oil
4-(2-methoxyphenyl)-N-(2-aminophenyl)-1-piperazinbutanamine Description 12

N-(2-Nitrophenyl)-4-(3-trifluoromethylphenyl)-1-
piperazinpropionamide

The compound was prepared from 3-bromo-N-(2-nitrophenyl)propionamide and 1-(3-trifluoromethylphenyl)piperazine according to the method described in J. Med. Chem. 33, 2970 (1990). Monohydrochloride salt. M.p. 185°–188° C.

Description 13

N-(2-Aminophenyl)-4-(3-trifluoromethylphenyl)-1-piperazinpropionamide

The compound was prepared according to the method described in J. Med. Chem. 30, 13 (1987) by catalytic reduction of N-(2-nitrophenyl)-4-(3-trifluoromethylphenyl)-1-piperazin propionamide in the presence of 10% Pd/C. Monohydrochloride salt. M.p. 194°–196° C.

Example 3

N-[3-(4-(3-trifluoromethylphenyl)piperazin-1-yl)propionyl]-2,3-dihydro-1H-benzimidazol-2-one (Compound 21)

A solution of N-(2-aminophenyl)-4-(3-trifluoromethylphenyl)-1-piperazinpropionamide (4 g) and triethylamine (2 ml) in anhydrous tetrahydrofurane (50 ml) was dropped to a solution of trichloromethylchloroformate (1 ml) in tetrahydrofurane (20 ml) under stirring at 5° C. When the addition was finished, the reaction was allowed to reach the room temperature and the stirring was continued for 1 hour. Then water was added and the product was extracted with ethyl acetate. After evaporating the solvent, the residue was purified by column chromatography over silica gel and a mixture of $CH_2Cl_2$, MeOH, $NH_3$ 90/10/1 as eluent. 1.8 g of the desired product were obtained. The hydrochloride was obtained from ethanol-diethyl ether. Hydrochloride salt (ethanol-diethyl ether) M.p. 227°–230° C.

Analysis $C_{21}H_{21}F_3N_4O_2$ . HCl Found % C 54,65 H 4,76 N 12,10 Calc. % C 55,45 H 4,88 N 12,32 $^1$H NMR (DMSO-$d_6$/CDCL$_3$ 5:2) 11.43 (s, 1H), 10.84 (b, 1H), 8.02 (m, 1H), 7.6–7.0 (7H), 4.1–3.2 (12H)

Similarly and using the suitable intermediates the following compounds were obtained:

6-chloro-1-[4-(4-(2-methoxyphenyl)piperazin-1-yl)butyl]-2,3-dihydro-1H-benzimidazol-2-one (Compound 26)

Hydrochloride salt (diethyl ether) M.p. 206°–209° C.

Analysis $C_{22}H_{27}ClN_4O_2$ . 2HCl Found % C 54,11 H 6,08 N 10,82 Calc. % C 54,16 H 5,99 N 11,48 $^1$H NMR (DMSO-$d_6$/CDCL$_3$ 5:2) 10.98 (s, 1H), 10.54 (b, 1H), 7.3–6.8 (8H), 3.81 (s, 3H), 4.0–3.0 (12H), 2.0–1.6 (4H)

5,6-dichloro-1-[4-(4-(2-methoxyphenyl)piperazin-1-yl)butyl]-2,3-dihydro-1H-benzimidazol-2-one (Compound 27)

Hydrochloride salt (diethyl ether) M.p. 157°–160° C.

Analysis $C_{22}H_{26}Cl_2N_4O_2$ . 2HCl Found C 50,19 H 5,60 N 10,52 Calc. % C 50,59 H 5,40 N 10,73 $^1$H NMR (DMSO-$d_6$/CDCL$_3$ 5:2) 11.16 (s, 1H), 10.75 (b, 1H), 7.42 (s, 1H), 7.13 (s, 1H), 7.2–6.7 (5H), 3.82 (s, 3H), 4.0–3.0 (12H), 2.1–1.6 (4H)

6-methyl-1-[4-(4-(2-methoxyphenyl)piperazin-1-yl)butyl]-2,3-dihydro-1H-benzimidazol-2-one (Compound 28)

Hydrochloride salt (isopropanol) M.p. 210°–213° C.

Analysis $C_{23}H_{30}N_4O_2$ . 2HCl Found % C 59,53 H 7,19 N 11,68 Calc. % C 59,10 H 6,90 N 11,99 $^1$H NMR (DMSO-$d_6$/CDCL$_3$ 5:2) 10.98 (b, 1H), 10.66 (s, 1H), 7.08 (b, 1H), 7.1–6.7 (7H), 3.82 ( S, 3H), 3.9–3.0 (12H), 2.35 (s, 3H), 2.1–1.7 (4H)

1-[4-(4-(2-methoxyphenyl)piperazin-1-yl)butyl]-2,3-dihydro-1H-benzimidazol-2-one (Compound 1)

M.p. 159°–161° C.

Analysis $C_{22}H_{28}N_4O_2$ Found % C 69,30 H 7,50 N 14,50 Calc. % C 69,45 H 7,42 N 14,73 $^1$H NMR (CDCL$_3$) 9.82 (s, 1H), 7.1–6.7 (8H), 3.93 (t, 2H), 3.84 (S, 3H), 3.1–2.9 (4H), 2.8–2.5 (4H), 2.45 (t, 2H), 1.9–1.4 (4H)

Description 14

1-(4-Chlorobutyl)-4-(3-trifluoromethylphenyl)-piperazine

The product was prepared according to the methods described in J. Org. Chem. 24, 764 (1958) from 1-(3-trifluoromethylphenyl)piperazine and 1-chloro-4-bromobutane. The compound was used as such without further purification.

Analogously may be prepared:
1-(6-Chlorohexyl)-4-(3-trifluoromethylphenyl)piperazine
1-(4-Chlorobutyl)-4-(2-methoxyphenyl)piperazine
1-(4-Chlorobutyl)-4-(3-chlorophenyl)piperazine

Example 4

1-[4-(4-(3-chlorophenyl)piperazin-1-yl)butyl]-3-methyl-2,3-dihydro-1H-benzimidazol-2-one (Compound 17)

To a suspension of 80% sodium hydride (1 g) in anhydrous dimethylformamide (50 ml) 1-methyl-benzimidazol-2-one (5 g) was added portionwise. After stirring the reaction mixture for 1 hour at room temperature, a solution of 4-(3-chlorophenyl)-1-chlorobutyl-piperazine (6 g) in dimethylformamide (15 ml) was added. The reaction mixture was allowed to react for 10 hours at 60° C., then after cooling, water was added and the product was extracted with ethyl acetate. The raw product was purified by column chromatography over silica gel and a mixture $CH_2Cl_2$/MeOH 95/5 as eluent. 5 g of the desired product were obtained.

Hydrochloride salt (isopropanol) M.p. 213°–216° C.

Analysis $C_{22}H_{27}ClN_4O$ . HCl Found % C 60,65 H 6,53 N 12,34 Calc. % C 60,69 H 6,48 N 12,87 $^1$H NMR (CDCL$_3$) 12.84 (b, 1H), 7.3–6.7 (8H), 3.93 (t, 2H), 3.42 (s, 3H), 4.0–2.9 (10H), 2.1–1.8 (4H)

Analogously were obtained:

1-[4-(4-(3-trifluoromethyl-phenyl)piperazin-1-yl)butyl]-3-methyl-2,3-dihydro-1H-benzimidazol-2-one (Compound 9)

Hydrochloride salt (isopropanol) M.p. 215°–216° C.

Analysis $C_{23}H_{27}F_3N_4O$ . HCl Found % C 58,74 H 6,08 N 12,03 Calc. % C 58,91 H 6,02 N 11,95 $^1$H NMR (DMSO-$d_6$/CDCL$_3$ 5:2) 10.81 (b, 1H), 7.5–6.9 (8H), 3.90 (t, 2H), 3.36 (s, 3H), 4.1–3.0 (10H), 2.0–1.6 (4H)

1-[6-(4-(3-trifluoromethyl-phenyl)piperazin-1-yl)hexyl]-3-ethyl-2,3-dihydro-1H-benzimidazol-2-one (Compound 13)

Hydrochloride salt (isopropanol) M.p. 136°–139° C.

Analysis $C_{26}H_{33}F_3N_4O \cdot HCl$ Found % C 60,89 H 6,51 N 11,03 Calc. % C 61,11 H 6,71 N 10,96 $^1H$ NMR (CDCL$_3$) 12.91 (b, 1H), 7.4–6.8 (8H), 4.1–2.8 (14H), 1.33 (t, 3H), 2.2–1.2 (8H)

1-[4-(4-(2-methoxyphenyl)piperazin-1-yl)butyl]-3-allyl-2,3-dihydro-1H-benzimidazol-2-one (Compound 14)

Hydrochloride salt (isopropanol) M.p. 201°–204° C.

Analysis $C_{25}H_{32}N_4O_2 \cdot 2HCl$ Found % C 60,50 H 6,59 N 11,53 Calc. % C 60,85 H 6,94 N 11,35 $^1H$ NMR (DMSO-d$_6$/CDCL$_3$ 5:2) 11.07 (b, 1H), 8.04 ( s, 1H +HDO), 7.2–6.8 (8H), 5.90 (m, 1H), 5.2–5.0 (2H), 4.48 (d, 2H), 3.92 (t, 2H), 3.82 (s, 3H), 3.7–3.0 (10H), 2.0–1.7 (4H)

1-[4-(4-(3-trifluoromethyl-phenyl)piperazin-1-yl)butyl]-3-isopropyl-2,3-dihydro-1H-benzimidazol-2-one (Compound 15)

Hydrochloride salt (isopropanol) M.p. 181°–184° C.

Analysis $C_{25}H_{31}F_3N_4O \cdot HCl$ Found % C 60,00 H 6,69 N 11,01 Calc. % C 60,42 H 6,49 N 11,27 $^1H$ NMR (CDCL$_3$) 12.85 ( b, 1H ), 7.4–6.9 (8H), 4.70 (m, 1H), 3.92 (t, 2H), 4.0–2.8 (10H), 2.2–1.8 (4H), 1.53 (d, 6H)

1-[4-(4-(3-chlorophenyl)piperazin-1-yl)butyl]-3-n-hexyl-2,3-dihydro-1H-benzimidazol-2-one (Compound 16)

Hydrochloride salt (isopropanol) M.p. 107°–111° C.

Analysis $C_{27}H_{37}ClN_4O \cdot HCl$ Found % C 63,87 H 7,37 N 11,27 Calc. % C 64,15 H 7,58 N 11,08 $^1H$ NMR (CDCL$_3$) 12.80 (b, 1H), 7.2–6.5 (8H), 3.9–2.7 (14H), 2.3–1.2 (12H), 0.87 (m, 3H)

Description 15

1-(4-aminobutyl)-4-(3-trifluoromethyl-phenyl)-piperazine

Litium aluminium hydride (1 g) was suspended in 30 ml of anhydrous tetrahydrofurane. 4-[4-(3-trifluoromethylphenyl)piperazin-1-yl]butirronitrile (5,4 g) dissolved in 30 ml of the same solvent was dropped into the suspension of the reducing agent under stirring by cooling at 5° C. Finally, the temperature was allowed to reach the room temperature and the suspension was stirred for all over might. An amount of water, necessary to decompose the reaction complexes, was added. The unsoluble material was eliminated by filtration and the residual organic solution was concentrated to dryness under vacuum. The product was purified by column chromatography on 60 Merck silica gel with eluent: methylene chloride/methanol/32% ammonium hydroxide 80:20:2. 2,3 g of a colourless oil were obtained.

Analogously may be prepared:

1-(2-aminoethyl)-4-(2-pyrimidinyl)-piperazine. Oil 1-(2-aminoethyl)-4-(3-trifluoromethyl)phenyl-piperazine. Oil

Example 5

N-[2-(4-(3-trifluoromethyl-phenyl)piperazin-1-yl)ethyl]-2-oxo-2,3-dihydro-1H-benzimidazol-1-carboxamide (Compound 32)

A mixture of 1-chlorocarbonyl-benzimidazol-2-one (1 g) prepared as described in EP 309423 and 4-(3-trifluoromethylphenyl)-1-(2-aminoethyl)piperazine (3,2 g) with Na$_2$CO$_3$ (1,57 g) in anhydrous dimethylformamide (50 ml) was heated with stirring at 100 ° C. for 4 hours. The reaction mixture was cooled, diluted with water and extracted with ethyl acetate. After removal of the solvent, the residual solid was converted into the corresponding hydrochloride salt by adding anhydrous hydrogen chloride to a solution of the base in isopropanol. 1,3 g of the desired compound were obtained. Hydrochloride salt (isopropanol) M.p. 230°–233° C.

Analysis $C_{21}H_{22}F_3N_5O_2 \cdot HCl$ Found % C 53,51 H 4,92 N 14,99 Calc. % C 53,68 H 4,93 N 14,90 $^1H$ NMR (DMSO-d$_6$/CDCL$_3$ 5:2) 11.60 (s, 1H), 10.80 (b, 1H), 9.01 (t, 1H), 8.00 (m, 1H), 7.5–6.6 (7H), 4.0–2.8 (12H)

Analogously may be obtained:

N-[2-(4-(3-trifluoromethyl-phenyl)piperazin-1-yl)butyl]-2-oxo-2,3-dihydro-1H-benzimidazol-1-carboxamide (Compound 33) $^1H$ NMR (DMSO-d$_6$/CDCL$_3$ 5:2) 11.57 (s, 1H), 11.09 (b, 1H), 8.83 (t, 1H), 7.98 (m, 1H), 7.6–7.0 (7H), 4.1–3.0 (12H), 2.1–1.6 (4H)

Similarly, starting from 3-methyl-1-chlorocarbonylbenzimidazol-2-one, prepared as described in EP 309,423, it was obtained

N-[2-(4-(3-trifluoromethyl-phenyl)piperazin-1-yl)ethyl]-2-oxo-3-methyl-2,3-dihydro-1H-benzimidazol-1-carboxamide (Compound 34)

Hydrochloride salt (isopropanol) M.p. 214°–215° C.

Analysis $C_{22}H_{24}F_3N_5O_2 \cdot HCl$ Found % C 54,40 H 5,25 N 14,39 Calc. % C 54,60 H 5,21 N 14,47 $^1H$ NMR (DMSO-d$_6$) 10.72 (b, 1H), 8.96 (t, 1H), 8.04 (d, 1H), 7.47 (m, 1H), 7.4–7.1 (6H), 3.41 (s, 3H), 4.1–3.1 (12H)

Example 6

1-[4-(4-(3-trifluoromethyl-phenyl)piperazin-1-yl)butyl]-3-isopropyl-2,3-dihydro-1H-benzimidazol-2-one (Compound 15)

1-[4-(4-(3-Trifluoromethyl-phenyl)-piperazin-1-yl)butyl]-2,3-dihydro-1H-benzimidazol-2-one (1 g) was added portionwise to a suspension of 85% powdered potassium hydroxide (0,24 g) in dimethylformamide, under stirring at room temperature. The addition was completed in 10 minutes and the reaction mixture so obtained was stirred at the same temperature for 1 hour. Then, isopropylbromide (0,27 ml) was added and heated for 5 hours at 40° C. The reaction mixture was poured in water and the product was extracted with ethyl acetate. For concentration to dryness the desired product as residual solid was obtained. It was purified by preparing the hydrochloride salt from ethyl acetate. Hydrochloride salt M.p. 181°–184° C.

Analysis $C_{25}H_{31}F_3N_4O \cdot HCl$ Found % C 60,31 H 6,48 N 11,20 Calc. % C 60,42 H 6,49 N 11,27 $^1$H NMR (CDCL$_3$) 12.85 (b, 1H), 7.4–6.9 (8H), 4.70 (m, 1H), 3.92 (t, 2H), 4.0–2.8 (10H), 2.2–1.8 (4H), 1.53 (d, 6H)

Analogously were prepared:

1-[6-(4-(3-trifluoromethyl-phenyl)piperazin-1-yl)hexyl]-3-ethyl-2,3-dihydro-1H-benzimidazol-2-one (Compound 13)

Hydrochloride salt (isopropanol) M.p. 138°–139° C.

Analysis $C_{26}H_{33}F_3N_4O \cdot HCl$ Found % C 61,32 H 6,70 N 10,91 Calc. % C 61,11 H 6,71 N 10,96 $^1$H NMR (CDCL$_3$) 12.91 (b, 1H), 7.4–6.8 (8H), 4.1–2.8 (14H), 1.33 (t, 3H), 2.2–1.2 (8H)

1-[4-(4-(2-methoxyphenyl)piperazin-1-yl)butyl]-3-allyl-2,3-dihydro-1H-benzimidazol-2-one (Compound 14)

Hydrochloride salt (isopropanol) M.p. 201°–204° C.

Analysis $C_{25}H_{32}N_4O_2 \cdot 2HCl$ Found % C 60,93 H 7,01 N 11,24 Calc. % C 60,85 H 6,94 N 11,35 $^1$H NMR (DMSO-d$_6$/CDCL$_3$ 5:2) 11.07 (b, 1H), 8.04 (s, 1H+HDO), 7.2–6.8 (8H), 5.90 (m, 1H), 5.2–5.0 (2H), 4.48 (d, 2H), 3.92 (t, 2H), 3.82 (s, 3H), 3.7–3.0 (10H), 2.0–1.7 (4H)

1-[4-(4(3-chlorophenyl)piperazin-1-yl)butyl]-3-n-hexyl-2,3-dihydro-1H-benzimidazol-2-one (Compound 16)

Hydrochloride salt (isopropanol) M.p. 108°–111° C.

Analysis $C_{27}H_{37}ClN_4O \cdot HCl$ Found % C 64,31 H 7,56 N 11,12 Calc. % C 64,15 H 7,58 N 11,08 $^1$H NMR (CDCL$_3$) 12.80 (b, 1H), 7.2–6.5 (8H), 3.9–2.7 (14H), 2.3–1.2 (12H), 0.87 (m, 3H)

1-[4-(4-(3-chlorophenyl)piperazin-1-yl)butyl]-3-methyl-2,3-dihydro-1H-benzimidazol-2-one (Compound 17)

Hydrochloride salt (isopropanol) M.p. 214°–216° C.

Analysis $C_{22}H_{27}ClN_4O \cdot HCl$ Found % C 60,51 H 6,53 N 12,81 Calc. % C 60,69 H 6,48 N 12,87 $^1$H NMR (CDCL$_3$) 12.84 (b, 1H), 7.3–6.7 (8H), 3.93 (t, 2H), 3.42 (s, 3H), 4.0–2.9 (10H), 2.1–1.8 (4H)

The following not limitative examples of pharmaceutical compositions according to the invention are given:

Example 7

| Tablets | |
|---|---|
| active ingredient | 10 mg |
| lactose | 187 mg |
| corn starch | 50 mg |
| magnesium stearate | 3 mg |

Method of preparation: the active ingredient, lactose and corn starch were mixed and homogeneously moistened with water. After screening of the moist mass and drying in a tray drier, the mixture was again passed through a screen and magnesium stearate was added. Then the mixture was pressed into tablets weighing 250 mg each. Each tablet contains 10 mg of active ingredient.

Example 8

| Capsules | |
|---|---|
| active ingredient | 10 mg |
| lactose | 188 mg |
| magnesium stearate | 2 mg |

Method of preparation: the active ingredient was mixed with the auxiliary products, and the mixture was passed through a screen and mixed homogeneously in a suitable device. The resulting mixture was filled into hard gelatine capsules (200 ml per capsule); each capsule contains 10 mg of active ingredient.

Example 9

| Ampoules | |
|---|---|
| active ingredient | 2 mg |
| sodium chloride | 9 mg |

Method of preparation: the active ingredient and sodium chloride were dissolved in an appropriate amount of water for injection. The resulting solution was filtered and filled into vials under sterile conditions.

Example 10

| Suppositories | |
|---|---|
| active ingredient | 25 mg |
| semisynthetic glicerides of fatty acids | 1175 mg |

Method of preparation: the semisynthetic glicerides of fatty acids were melted and the active ingredient was added while stirring homogeneously. After cooling at a proper temperature the mass was poured into preformed moulds for suppositories weighing 1200 mg each. Each suppository contains 25 mg of active ingredient.

Example 11

| Nasal spray | |
|---|---|
| active ingredient | 80 mg |
| benzalconchloride | 0,1 mg |
| sodium chloride | 8 mg |
| EDTA | 1 mg |
| sodium phosphate (buffer pH 6,5) | 10 mg |
| polysorbate 80 | 10 mg |
| bidistilled water | q.s. to 2 ml |

Method of preparation: the single components were added in the suitable volume of bidistilled water by stirring until a complete dissolution before an further addition. After taking to volume, the solution was filtered upon sterilising filter,

We claim:
1. A compound of formula I

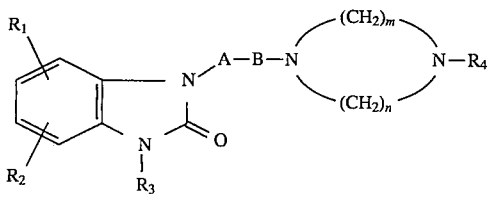

wherein $R_1$ and $R_2$ may each independently be a hydrogen atom, halogen, $C_{1-3}$ alkyl or $C_{1-3}$ alkoxy, R3 is hydrogen, $C_{1-3}$ alkyl or $C_{2-6}$ alkenyl A is —CO— or —CONH— or it is absent;

B is a straight chain $C_{2-6}$ alkyl;

m and n are both the integer 2;

$R_4$ is phenyl, naphtyl, benzodioxanyl, or pyrimidinyl, each being optionally substituted by one substituent selected from halogen, trifluoromethyl, $C_{1-3}$ alkoxy, or a physiologically acceptable acid addition salt thereof.

2. Compounds of formula (I) according to claim 1 characterized in that A is absent, B is a straight, saturated $C_{2-4}$ alkyl, m and n are the integer 2, $R_4$ is a substituted phenyl ring wherein the substituents are selected from methoxy, chloro or trifluoromethyl, and acid addition salts thereof.

3. Compound of formula (I) selected from
1-[2-(4-(3-trifluoromethyl-phenyl)piperazin-1-yl)ethyl]-2,3-dihydro-1H-benzimidazol-2-one
1-[4-(4-(3-chloro-phenyl)piperazin-1-yl) butyl]-2,3-dihydro-1H-benzimidazol-2-one
1-[4-(4-(3-trifluoromethyl-phenyl)piperazin-1-yl)butyl]-2,3-dihydro-1H-benzimidazol-2-one
1-[4-(4-(3-trifluoromethyl-phenyl)piperazin-1-yl)butyl]-3-methyl-2,3-dihydro-1H-benzimidazol-2-one
1-[4-(4-(3-trifluoromethylphenyl)piperazin-1-yl)butyl]-3-isopropil-2,3-dihydro-1H-benzimidazol-2-one
1-[3-(4-(3-trifluoromethyl-phenyl)piperazin-1-yl)propyl]-2,3-dihydro-1H-benzimidazol-2-one
6-methoxy-1-[4-(4-(3-trifluoromethyl-phenyl)piperazin-1-yl)butyl]-2,3-dihydro-1H-benzimidazol-2-one
1-[4-(4-(1-naphtyl)piperazin-1-yl)butyl]-2,3-dihydro-1H-benzimidazol-2-one.

4. Salts according to claim 1, characterized in that the physiologically acceptable acids are hydrochloric, maleic or fumaric acid.

5. Pharmaceutical compositions for the use in the treatment of patients suffering from depression, bipolar disorder, anxiety, sleep and sexual disorder, psychosis, schizophrenia, personality disorders, mental organic disorders, mental disorders in childhood, aggressiveness and age associated memory impairment, comprising as active ingredient a pharmaceutically effective amount of a compound of formula (I), as defined in claim 1 or physiologically acceptable acid additional salts thereof, in association with pharmaceutically acceptable carriers, diluents or excipients.

6. Pharmaceutical compositions for the use in the treatment of patients suffering from hypertension and thrombosis, comprising as active ingredient a therapeutically effective amount of a compound as defined in claim 1, or physiologically acceptable acid addition salts thereof, in association with pharmaceutically acceptable carriers, diluents or excipients.

* * * * *